US011712343B2

(12) United States Patent
Predick et al.

(10) Patent No.: US 11,712,343 B2
(45) Date of Patent: *Aug. 1, 2023

(54) LATERAL SPINE PLATE WITH COLLAPSIBLE VERTEBRAL ATTACHMENT ARMS

(71) Applicant: Life Spine, Inc., Huntley, IL (US)

(72) Inventors: Daniel P. Predick, West Lafayette, IN (US); Garrett D. Lauf, Elgin, IL (US)

(73) Assignee: Life Spine, Inc., Huntley, IL (US)

( * ) Notice: Subject to any disclaimer, the term of this patent is extended or adjusted under 35 U.S.C. 154(b) by 149 days.

This patent is subject to a terminal disclaimer.

(21) Appl. No.: 17/093,202

(22) Filed: Nov. 9, 2020

(65) Prior Publication Data

US 2021/0068976 A1    Mar. 11, 2021

Related U.S. Application Data

(63) Continuation of application No. 15/958,278, filed on Apr. 20, 2018, now Pat. No. 10,849,763.

(60) Provisional application No. 62/487,699, filed on Apr. 20, 2017.

(51) Int. Cl.
| | |
|---|---|
| *A61F 2/44* | (2006.01) |
| *A61B 17/70* | (2006.01) |
| *A61B 17/86* | (2006.01) |
| *A61B 17/80* | (2006.01) |
| *A61F 2/30* | (2006.01) |

(52) U.S. Cl.
CPC ............ *A61F 2/4455* (2013.01); *A61B 17/70* (2013.01); *A61B 17/7059* (2013.01); *A61B 17/8605* (2013.01); *A61B 17/80* (2013.01); *A61F 2/442* (2013.01); *A61F 2002/305* (2013.01); *A61F 2002/30433* (2013.01); *A61F 2002/30471* (2013.01); *A61F 2002/30578* (2013.01)

(58) Field of Classification Search
CPC .................... A61F 2/442; A61F 2/4455; A61F 2002/30433; A61F 2002/30477; A61F 2002/30471; A61F 2002/305; A61F 2002/30578; A61F 2002/30329; A61F 2002/30331; A61B 17/70; A61B 17/7059; A61B 17/8605; A61B 17/80
USPC ........ 606/70–71, 280–299; 623/17.11–17.16
See application file for complete search history.

(56) References Cited

U.S. PATENT DOCUMENTS

| | | | |
|---|---|---|---|
| 8,343,223 B2 | 1/2013 | Bucci | |
| 8,852,278 B2 | 10/2014 | Bellas | |
| 9,180,022 B2 * | 11/2015 | Georges | ............... A61B 17/808 |

(Continued)

*Primary Examiner* — Jessica Weiss
(74) *Attorney, Agent, or Firm* — Foley & Lardner LLP (57) ABSTRACT

A lateral spine implant has a lateral spine cage and an associated lateral spine plate with one or more folding vertebral attachment arms, each arm configured for attachment to vertebral bone. The ability of the one or more arms to fold allows the lateral spine plate to be inserted/implanted at a lower profile height than traditional lateral spine plates. The lateral spine plate is meant to be used at times of intended or unintended compromise of the anterior longitudinal ligament (ALL) to prevent interbody cage migration, but may be adapted for any lateral plating application. Once expanded, each attachment arm is configured to receive a bone screw for securing the attachment arm to a vertebra, the bone screw retained by rotating cam lock nuts of the attachment arm.

16 Claims, 12 Drawing Sheets

(56) References Cited

U.S. PATENT DOCUMENTS

| | | | |
|---|---|---|---|
| 2008/0177390 A1* | 7/2008 | Mitchell | A61F 2/442 623/17.15 |
| 2008/0183294 A1* | 7/2008 | Adl | A61F 2/442 623/17.11 |
| 2008/0294262 A1* | 11/2008 | Levieux | A61F 2/4611 606/280 |
| 2010/0030334 A1* | 2/2010 | Molz, IV | A61F 2/4611 623/17.11 |
| 2010/0249937 A1 | 9/2010 | Blain et al. | |
| 2011/0015745 A1* | 1/2011 | Bucci | A61F 2/4455 623/17.16 |
| 2011/0224793 A1* | 9/2011 | Fortin | A61F 2/44 623/17.11 |
| 2013/0060288 A1* | 3/2013 | Rodgers | A61B 17/808 606/283 |
| 2013/0166027 A1* | 6/2013 | Bellas | A61F 2/447 623/17.16 |
| 2013/0345813 A1* | 12/2013 | Frank | A61B 17/8023 623/17.16 |
| 2014/0018922 A1* | 1/2014 | Marino | A61F 2/447 623/17.16 |
| 2014/0200670 A1* | 7/2014 | Chin | A61B 17/8023 623/17.16 |
| 2015/0297356 A1* | 10/2015 | Gamache | A61F 2/4611 623/17.16 |
| 2016/0000486 A1* | 1/2016 | Leduc | A61B 17/808 606/297 |
| 2016/0058481 A1* | 3/2016 | Blain | A61B 17/7059 606/279 |
| 2016/0213481 A1* | 7/2016 | Blain | A61F 2/4405 623/17.16 |
| 2017/0189077 A1* | 7/2017 | Blain | A61B 17/8042 |
| 2020/0375630 A1* | 12/2020 | Kim | A61F 2/447 623/17.16 |
| 2022/0000633 A1* | 1/2022 | Seifert | A61F 2/447 |

* cited by examiner

LATERAL SPINE PLATE WITH COLLAPSIBLE VERTEBRAL ATTACHMENT ARMS

CROSS-REFERENCE TO RELATED APPLICATIONS

This application is a continuation of U.S. application Ser. No. 15/958,278, filed Apr. 20, 2018, which claims the benefit of and/or priority under 35 U.S.C. § 119(e) to U.S. provisional patent application Ser. No. 62/487,699 filed Apr. 20, 2017 titled "Lateral Spine Plates With Collapsible Vertebral Attachment Arms," the entire contents of both applications are specifically incorporated herein by reference.

FIELD OF THE INVENTION

The present invention relates to orthopedic implants such as cages, plates, and screws for the spine and, more particularly to lateral spine cages having vertebral attachment capabilities.

BACKGROUND OF THE INVENTION

People contend with spine issues as a result of age, disease, trauma, and congenital and acquired complications and conditions. While some of these issues can be alleviated without surgery, other issues respond better to surgery. In some cases, such as vertebral fusion, surgery includes installing one or more orthopedic implants.

One type of orthopedic implant used in spinal fusion surgery is an interbody cage. The interbody cage is received in the disc space between adjacent vertebrae in order to facilitate and/or promote fusion between the adjacent vertebrae. Various interbody spine cages have been developed over the years. There are interbody cages for anterior introduction and placement into a disc space of the spine (AIF or Anterior Interbody Fusion), interbody cages for posterior introduction and placement into the disc space of the spine (PIF or Posterior Interbody Fusion), and interbody cages for lateral introduction and placement into the disc space of the spine (LIF or Lateral Interbody Fusion). Interbody cages are also attachable to a vertebra by one or more bone screws in order to inhibit and/or prevent the cage from moving after implantation.

As in most surgeries, one aim is to reduce trauma at the surgical site. To this end surgical procedures such as minimally invasive techniques are now used extensively. Orthopedic implants are often part of or a main goal of surgery. The size of an orthopedic implant has a bearing on the amount of trauma sustained at the implant site. Generally, the smaller the implant, the less trauma at the surgical site. It is therefore an object to provide an orthopedic implant that is minimal in size.

With laterally inserted spinal interbody cages, a spine plate may be used that allows attachment of the spine plate to a lateral side of a vertebra while the spinal interbody cage rests in the disc space. The lateral spine plate thus extends generally perpendicular to the longitudinal axis of the spinal interbody cage. The lateral spine plate spans the disc space along a lateral side(s) of the vertebra(e) and overlays a portion of either an upper or lower vertebra, or a portion of both an upper and lower vertebra in order to attach the lateral spine plate to the lateral side(s) of the vertebra(e) via bone screws. Such lateral spine plates are generally large and thus have a large profile, thereby increasing the chance of surgical trauma. It is apparent that it would be desirable to have a low profile lateral spine plate for a lateral interbody spine cage in order to reduce surgical trauma.

It is an object of the present invention to provide a lateral spine plate for a lateral interbody spine cage having a low surgical profile. It is further an object of the present invention to provide a lateral spine plate for a lateral interbody spine cage that overcomes the deficiencies of the prior art.

SUMMARY OF THE INVENTION

A lateral spine plate for a lateral spinal interbody cage has one or more collapsible/folding arms configured for attachment to one or more vertebrae, the ability of the one or more arms to collapse/fold allows the lateral spine plate to be inserted/implanted at a lower profile height than traditional lateral spine plates. The lateral spine plate is also modular respective to a standard spinal interbody cage allowing securement to the interbody cage when needed.

The present lateral spine plate is meant to be used at times of intended or unintended compromise of the anterior longitudinal ligament (ALL) to prevent interbody cage migration, but may be adapted for any lateral plating application.

Once expanded, each attachment arm is configured to receive a bone screw for securing the attachment arm to a vertebra, the bone screw retained by rotating cam lock nuts of the attachment arm.

The lateral spine plate has a hub with the one or two attachment arms each one pivotally connected to the hub. The hub has a bore that receives a pin for attaching the hub (plate) to the interbody cage.

In one form, the attachment pin has a compressible arrow tip that compresses within an insertion hole of the interbody cage and, upon reaching an inner wall of a window of the interbody cage, will expand and prevent disassociation. In one form, the shaft of the attachment pin includes threads that mate with threads of the insertion hole of the interbody cage to provide additional engagement with the interbody cage. The length of the attachment pin compressible arrow tip and threads provide the ability to adjust offset distance of the lateral spine plate from the interbody cage to allow for preferred placement of the interbody cage within the disc space and/or due to anatomical variations (e.g. osteophytes) that require accommodation.

In one form, the attachment pin has a threaded shaft for engaging the threads of the insertion hole of the interbody cage, but is sans a compressible arrow tip. Other variations are contemplated.

The central hub of the lateral spine plate preferably, but not necessarily, has a slot that receives the attachment pin and allows the threaded shaft thereof to translate anterior/posterior so that position of the lateral spine plate is not entirely dictated by placement of the interbody cage.

The central hub of the lateral spine plate may be configured to receive the attachment pin such that the threaded shaft thereof can translate in the cephalad/caudal direction in order to accommodate varying heights of the selected cage.

In one form, the collapsible/folding vertebral attachment arm is comprised of two translating members (in the cephalad/caudal direction) allowing the ability to accommodate varying heights of the interbody cage.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate forms of the present invention, wherein.

DETAILED DESCRIPTION OF THE INVENTION

Referring to FIGS. 1-7, there is depicted an exemplary form of a lateral spine plate, generally designated 14, adapted/configured to be connected, attached, or coupled to a lateral interbody spine cage, generally designated 12, Together, the lateral interbody spine cage 12 and the lateral spine plate 14 is a lateral spinal implant, generally designated 10. The lateral spinal implant 10 is made from a biocompatible material such as, but not limited to, titanium, stainless steel, or an alloy of titanium or steel. Other biocompatible materials may be used and are contemplated. The lateral spine plate implant 10 may be used for any portion of the spine.

The lateral spine plate 14 may be used generally with all types of lateral interbody spine cages not just with the lateral interbody spine cages shown and/or described herein. The lateral interbody spine cage 14 of the lateral spinal implant 10 is characterized by a generally rectangular body 22 defining a first end or nose 23 and a second end or rear 26, the nomenclature first and second being arbitrary. The nose 23 is inserted first into the interbody cavity/space during implantation and thus has a general curvature defining an upper (superior) curved surface 24 and a lower (inferior) curved surface 25. The rear 26 is generally planar having a slightly slanted upper (superior) surface 27 and a slightly slanted lower (inferior) surface 28. A first opening 29 is situated proximate the nose 23 while a second opening 30 is situated proximate the rear 26, the first and second openings 29, 30 separated by a bridge 31, the nomenclature first and second being arbitrary.

Figure 9:
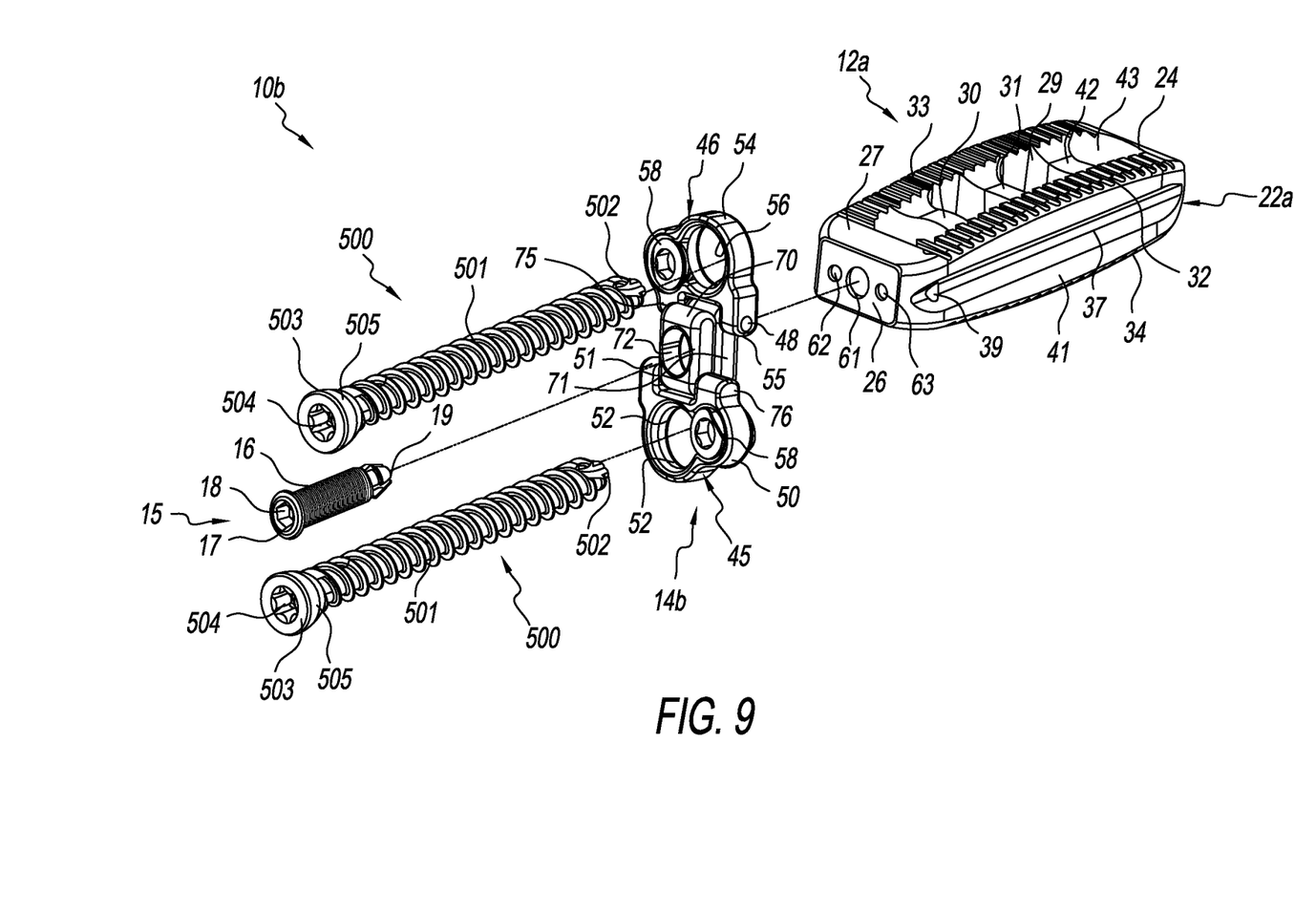
FIG. 9 is an exploded isometric view of another lateral spinal interbody cage with a lateral spine plate having collapsible vertebral attachment arms fashioned in accordance with the principles of the present invention, the vertebral attachment arms in an expanded or open position receiving bone screws and an attachment pin.

The body 22 and the first and second openings 29, 30 define a first upper (superior) side surface 32 having serrations, teeth or the like along its length, and a second upper (superior) side surface 33 having serrations, teeth or the like along its length, the nomenclature first and second being arbitrary. The body 22 and the first and second openings 29, 30 define a first lower (inferior) side surface 34 having serrations, teeth or the like along its length, and a second lower (inferior) side surface 35 having serrations, teeth or the like along its length, the nomenclature first and second being arbitrary. The body 22 further defines a first lateral side 40 having a longitudinal channel or groove 36 and a second lateral side 41 likewise having a longitudinal channel or groove 37, the nomenclature first and second being arbitrary. A bore opening 38 is provided in the first lateral side 40 proximate the rear 26 while a bore opening 39 is provided in the second lateral side 41 proximate the rear 26. As seen in FIG. 9 with respect to a spinal interbody cage variation 12a of the spinal interbody cage 12, but applicable to the spinal interbody cage 12, the rear 26 has an insertion hole 61 that is preferably, but not necessarily, be threaded. The rear 26 may also have first and second lateral holes 62, 63 (with the nomenclature first and second being arbitrary) on each side of the insertion hole 61, the first and second lateral holes 62, 63 being preferably, but not necessarily, smaller than the insertion hole 61. Thus describes a typical lateral interbody spine cage to which the present lateral spine plate 14 may be attached. The lateral spine plate 14 may be attached. to other lateral interbody spine cages such as shown and/or described herein, or otherwise.

Figure 1:
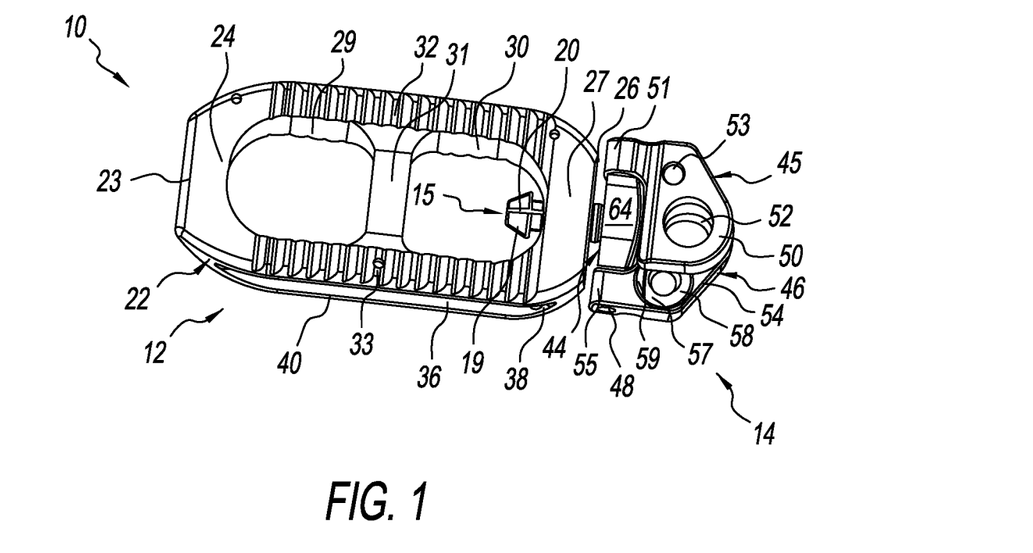
FIG. 1 is an isometric view of a lateral spinal interbody cage with a lateral spine plate having collapsible vertebral attachment arms fashioned in accordance with the principles of the present invention, the vertebral attachment arms in a collapsed or folded position.
Figure 2:
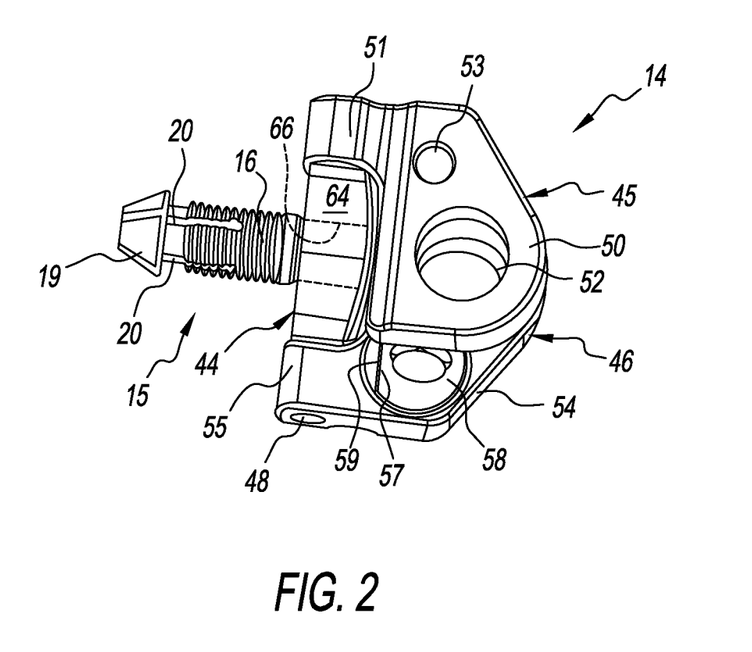
FIG. 2 is an isometric view of the lateral spine plate of FIG. 1 with its vertebral attachment arms in the collapsed or folded position.
Figure 3:
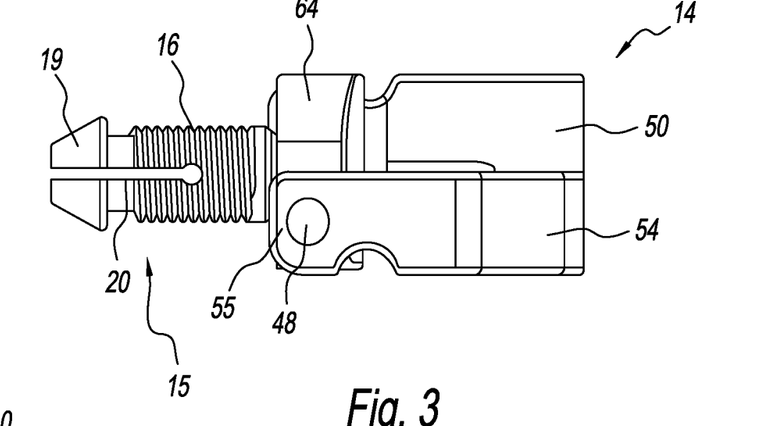
FIG. 3 is a side view of the lateral spine plate of FIG. 1 with its vertebral attachment arms in the collapsed or folded position.
Figure 4:
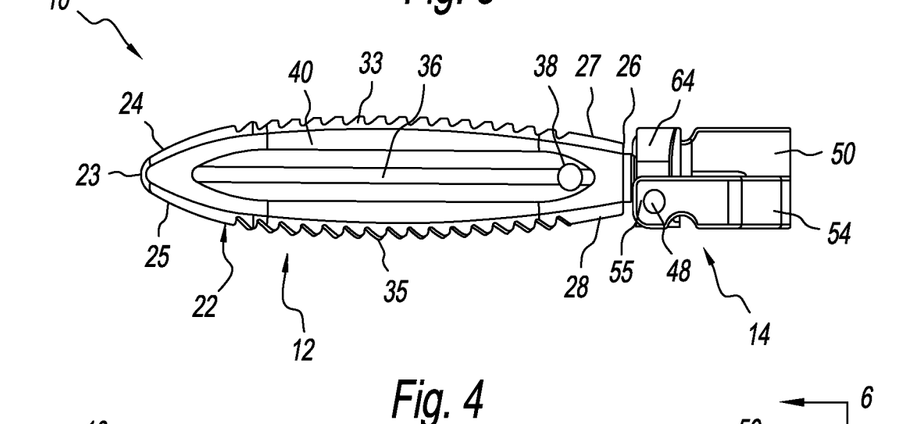
FIG. 4 is a side view of the lateral spinal interbody cage and lateral spine plate of FIG. 1 with the vertebral attachment arms of the lateral spine plate in the collapsed or folded position.
Figure 5:
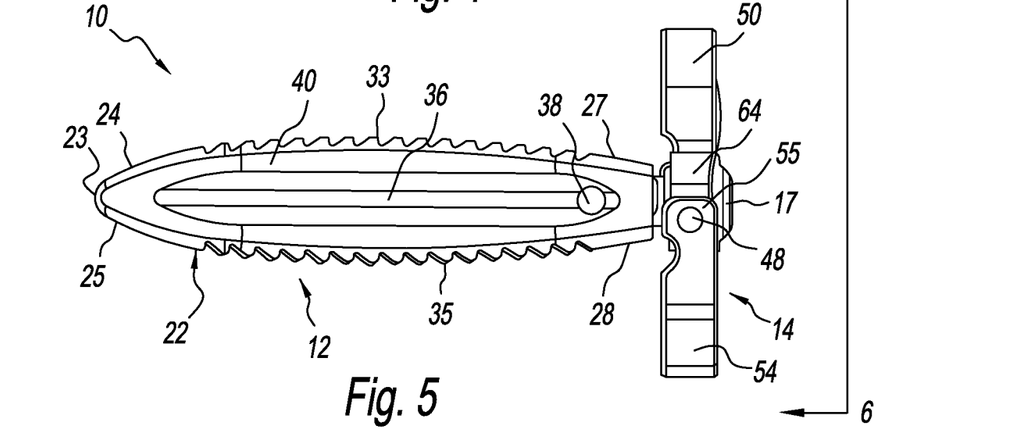
FIG. 5 is a side view of the lateral spinal interbody cage and lateral spine plate of FIG. 1 with the vertebral attachment arms of the lateral spine plate in an expanded or open position.

The lateral spine plate 14 has a central hub 44 defined by a generally rectangular body 64 having a bore 66 extending through the body 64 (see FIG. 2). The lateral spine plate 14 has a first, upper or superior vertebral attachment arm 45 and a second, lower or inferior vertebral attachment arm 46, the nomenclature first and second being arbitrary, each one configured for securement (attachment) to a vertebra via a bone screw 500. The first vertebral attachment arm 45 is defined by a body 50 having a bone screw bore 52 configured to accept and hold a bone screw 500, and a lock nut bore 53 with a lock nut 58. The body 50 further has a boss 51 at a rear side thereof that is pivotally connected to a side of the hub 44 via a hinge (not seen) such that the first attachment arm 45 can pivot or swing from or into a collapsed or folded position (e.g., FIGS. 1-4) to or from an expanded or open position (e.g. FIGS. 5-7). The second vertebral attachment arm 46 is defined by a body 54 having a bone screw bore 56 configured to accept and hold a bone screw 500, and a lock nut bore 57 with a lock nut 58. The body 54 further has a boss 55 at a rear side thereof that is pivotally connected to a side of the hub 44 via a hinge 48 such that the second attachment arm 46 can pivot or swing from or into a collapsed or folded position (e.g., FIGS. 1-4) to or from an expanded or open position (e.g. FIGS. 5-7). In this manner, the lateral spine plate 14 may be implanted in a collapsed or folded position to provide a low profile, then expanded or opened for attachment to the vertebrae.

The lateral spine plate 14 is connected to the lateral interbody cage 12 via an attachment pin 15. In one form, the attachment pin 15 has a threaded shaft 16, a head 17 with a configured socket 18, and an arrow tip 19. Slots 20 are formed in the tip 19 and through a portion of the threaded shaft 16 to provide compressibility of the arrow tip 19. The compressible arrow tip 19 compresses within the insertion hole 60 of the lateral interbody spine cage 12 and, upon reaching an inner wall of the opening 30 of the lateral interbody spine cage, expands and prevents disassociation (see FIG. 1). The threaded shaft 16 of the attachment pin 15 mate with threads of the insertion hole 60 of the lateral interbody spine cage 12 to provide additional engagement with the lateral interbody spine cage 12. The length of the attachment pin 15 provides the ability to adjust offset distance of the lateral spine plate from the interbody cage to allow for preferred placement of the interbody cage within the disc space and/or due to anatomical variations (e.g. osteophytes) that require accommodation.

Figure 6:
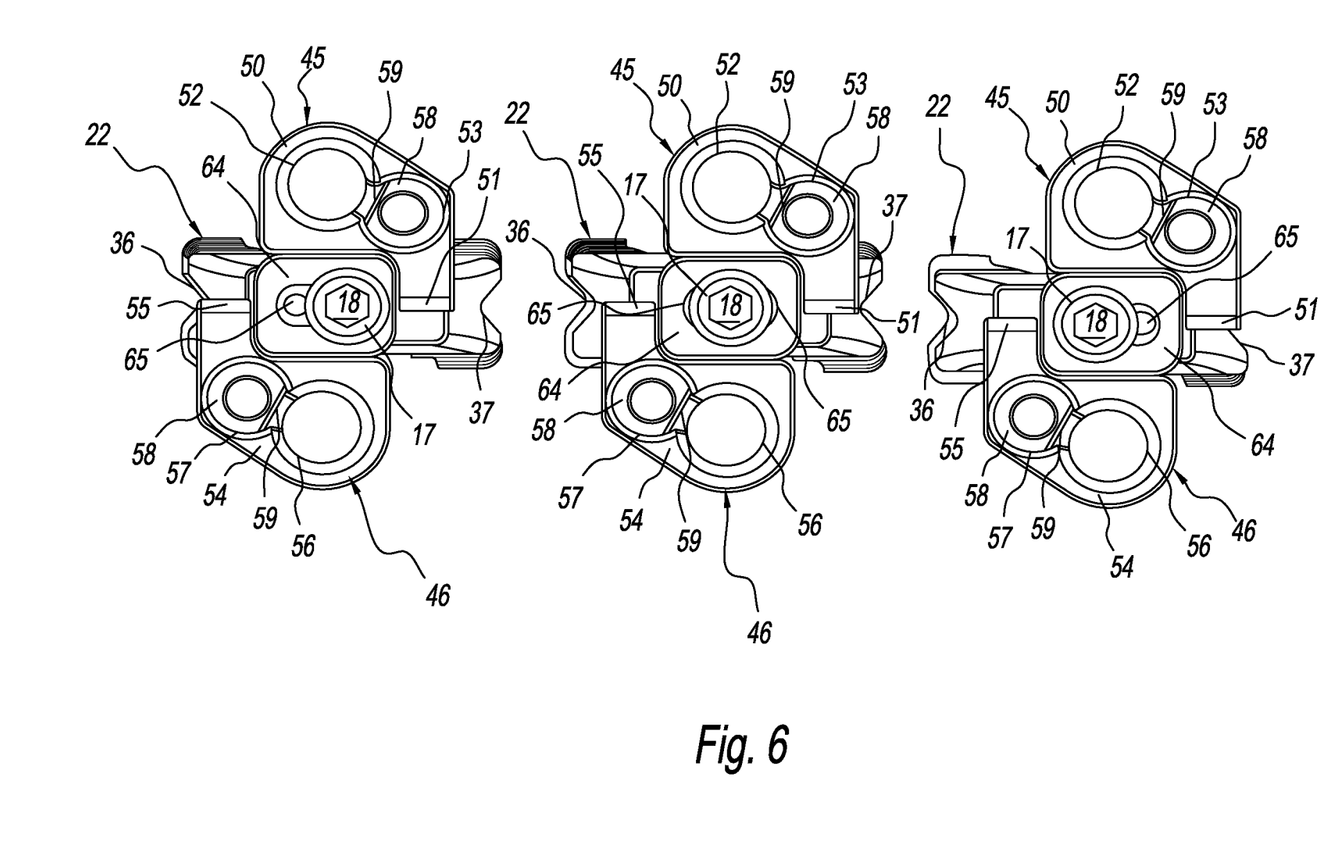
FIG. 6 is a series of end views of the lateral spinal interbody cage and lateral spine plate of FIG. 5 taken along line 6-6 thereof illustrating adjustability of the lateral spine plate relative to the lateral spinal interbody cage.
Figure 7:
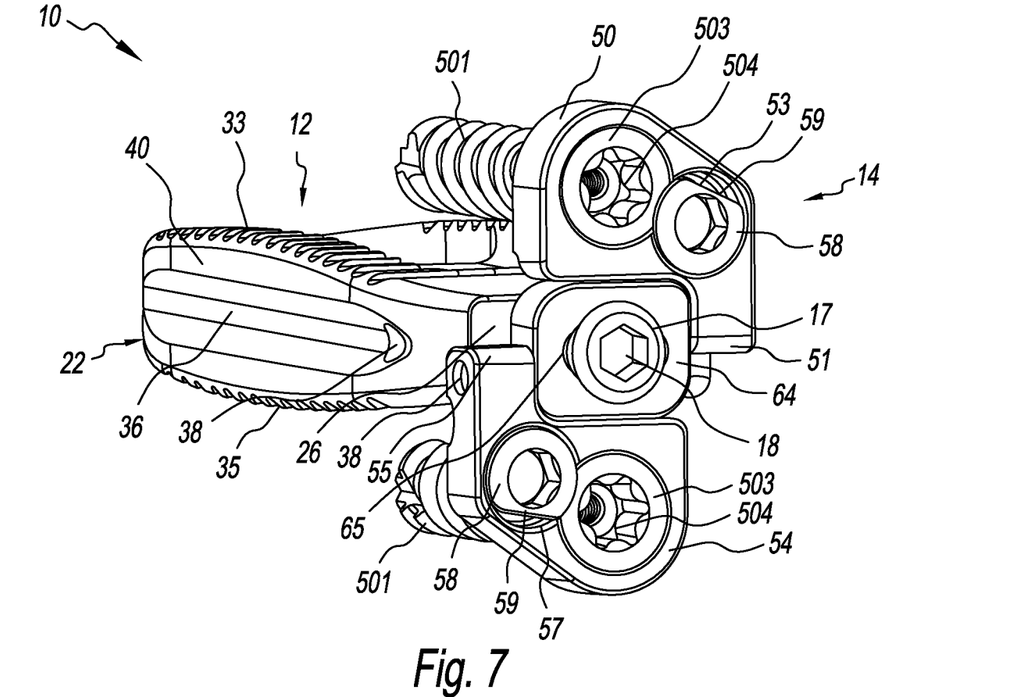
FIG. 7 is a rear side isometric view of the lateral spinal interbody cage and lateral spine plate of FIG. 1 with the vertebral attachment arms of the lateral spine plate in the extended or open position, bone screws received in each vertebral attachment arm and bone screw lock nuts in a locked position.

As depicted in FIG. 6, the bore 66 of the hub is preferably, but not necessarily, slotted (shown in FIG. 6 as an elongated slot 65) to allow the threaded shaft 16 of the attachment pin 15 to translate anterior/posterior relative to the lateral interbody spine cage 12 so that position of the lateral spine plate 14 is not entirely dictated by placement of the lateral interbody spine cage 12. FIG. 6 depicts three positions of the lateral spine plate 14 relative to the lateral interbody cage 12 illustrating the anterior/posterior translation capability.

The lateral spine plate 14 is attached to a vertebra by two bone screws 500, one bone screw 500 for each vertebral attachment arm. A bone screw 500 is characterized by a head 503 having a socket 504 in the top. The socket 504 is configured for receipt of a like-configured instrument or tool (not shown) for driving/installing the bone screw 500. The bone screw 500 has a shank 501 with external threads/threading configured for receipt in a vertebral body. The threaded shank 501 terminates in a distal tip 502.

As indicated above, the first attachment arm 45 has a lock nut 58 disposed in the bore 53, and the second attachment arm 46 has a lock nut 58 disposed in the bore 57. The bore 53 of the first attachment arm 45 is adjacent the bone screw bore 52 as the lock nut 58 is used to prevent the bone screw 500 that is in the bone screw bore 52 from backing or coming out of the bone screw bore once the bone screw 500 has been received therein—therefore locking the bone screw 500 in the bone screw bore 52. The lock nut 58 has a round perimeter or rim with a flat, cutout or the like (flat) 59 along a portion thereof. The lock nut 58 is rotatable in the bore such that the flat 59 may be oriented in any rotational position. When the flat 59 is in a rotational position where the flat is adjacent the bone screw bore 52 (see FIG. 6), the bone screw bore 52 is "open" such that a bone screw head 17 is receivable in the bone screw bore 52. When the lock nut 58 is a rotational position wherein the flat 59 is not adjacent the bone screw bore, the perimeter/rim of the lock nut 58 partially covers the bone screw bore and thus the bone screw head 17 (see FIG. 7). The perimeter/rim of the lock nut also provides a cam function relative to the bone screw head in order to lock the bone screw 500 relative to the first attachment arm 46. The bore 57 of the second attachment arm 46 is adjacent the bone screw bore 57 as the lock nut 58 is used to prevent the bone screw 500 that is in the bone screw bore 57 from backing or coming out of the bone screw bore once the bone screw 500 has been received therein—therefore locking the bone screw 500 in the bone screw bore 52 in the same manner as described with respect to the first attachment arm 45.

Figure 8:
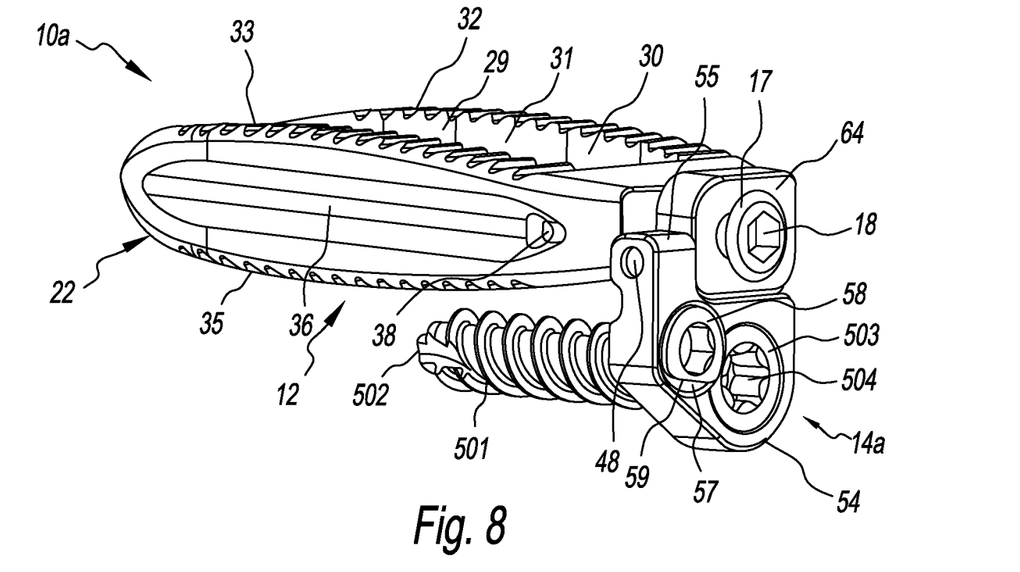
FIG. 8 is an isometric view of the lateral spinal interbody cage of FIG. 1 with a lateral spine plate having a single vertebral attachment arm with a bone screw received in the vertebral attachment arm and a bone screw lock nut in a locked position.

Referring to FIG. 8, there is depicted another exemplary form of a lateral spine plate, generally designated 14a, being a variation of the lateral spine plate 14, the lateral spine plate 14a shown connected to the lateral interbody spine cage 12 together forming a lateral spine implant 10a. The components, features, etc. of the lateral spine plate 14a that are the same as the lateral spine plate 14 have the same numbers as the lateral spine plate 14 while the those components, features, etc. that are different have the designation "a" after the number. The lateral spine plate 14a of FIG. 8 has a single vertebral attachment arm 54, here shown as the lower or inferior attachment arm 54, rather than the two vertebral attachment arms of the lateral spine plate 14.

Figure 10:
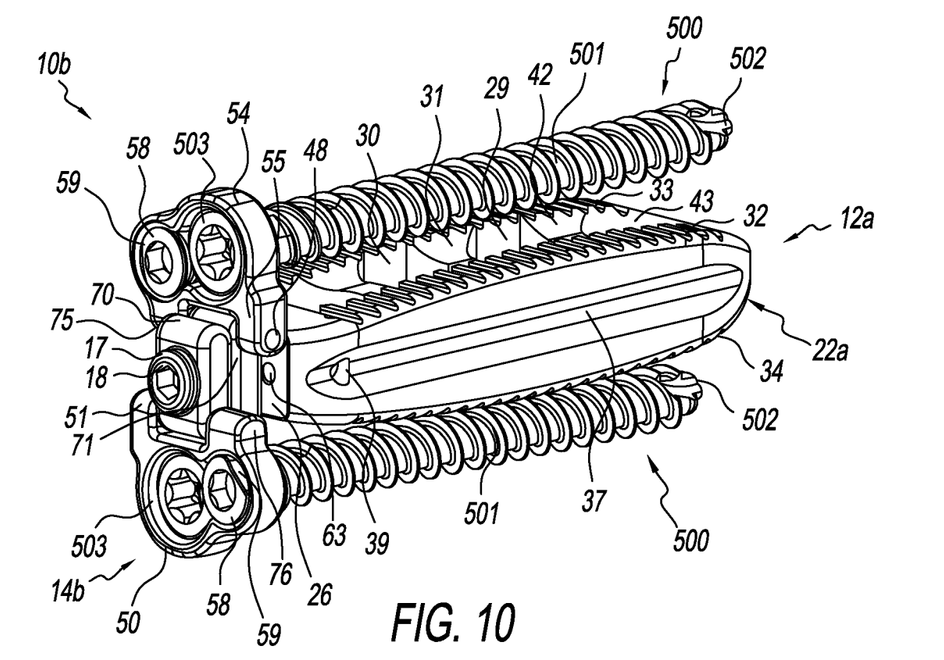
FIG. 10 is an isometric view of the lateral spinal interbody cage and lateral spine plate of FIG. 9, assembled via the attachment pin, with both vertebral attachment arms in the extended or open position, the bone screws received therein, and the bone screw nuts in the locked position.
Figure 11:
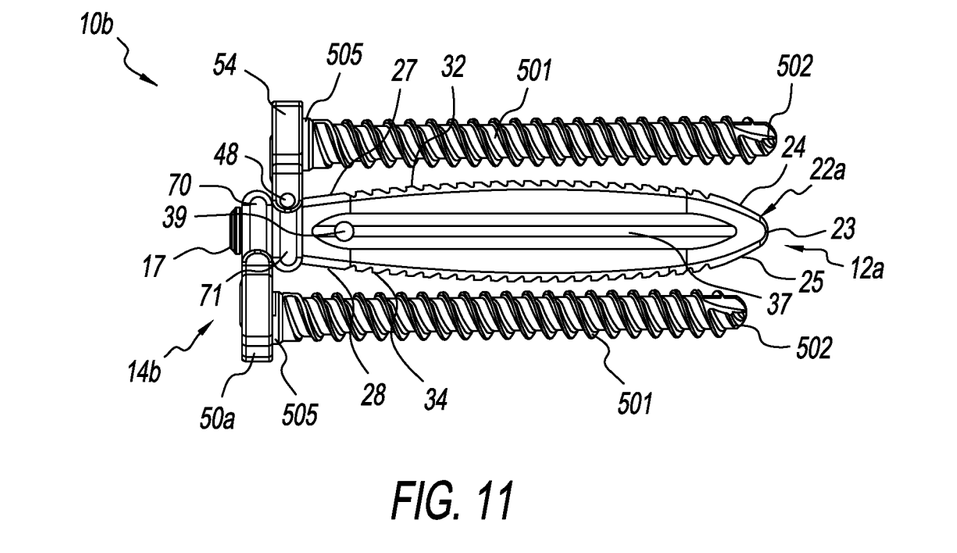
FIG. 11 is a side view of the lateral spinal interbody cage and lateral spine plate of FIG. 10.
Figure 12:
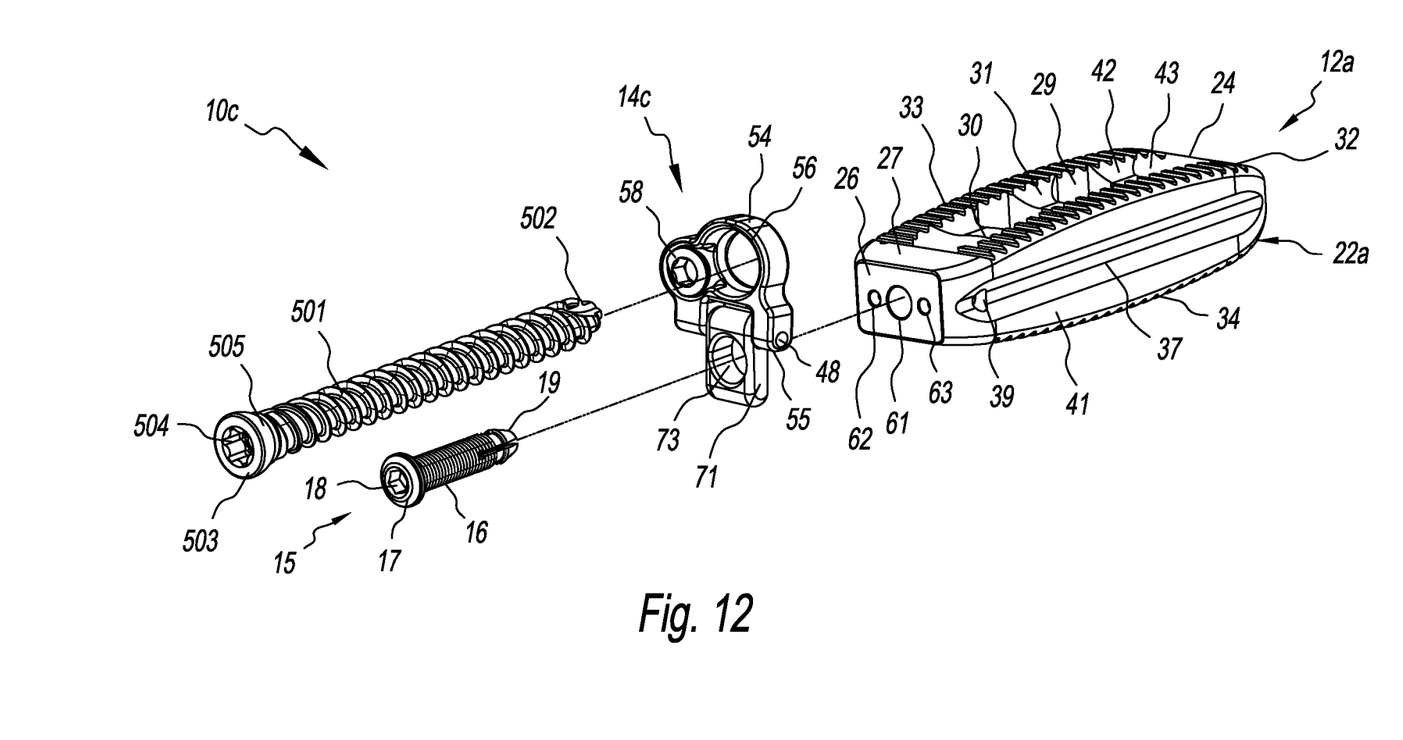
FIG. 12 is an exploded view of another lateral spinal interbody cage with a lateral spine plate having a single collapsible vertebral attachment arm fashioned in accordance with the principles of the present invention, the vertebral attachment arm in an expanded or open position and receiving a bone screw and attachment pin.
Figure 13:
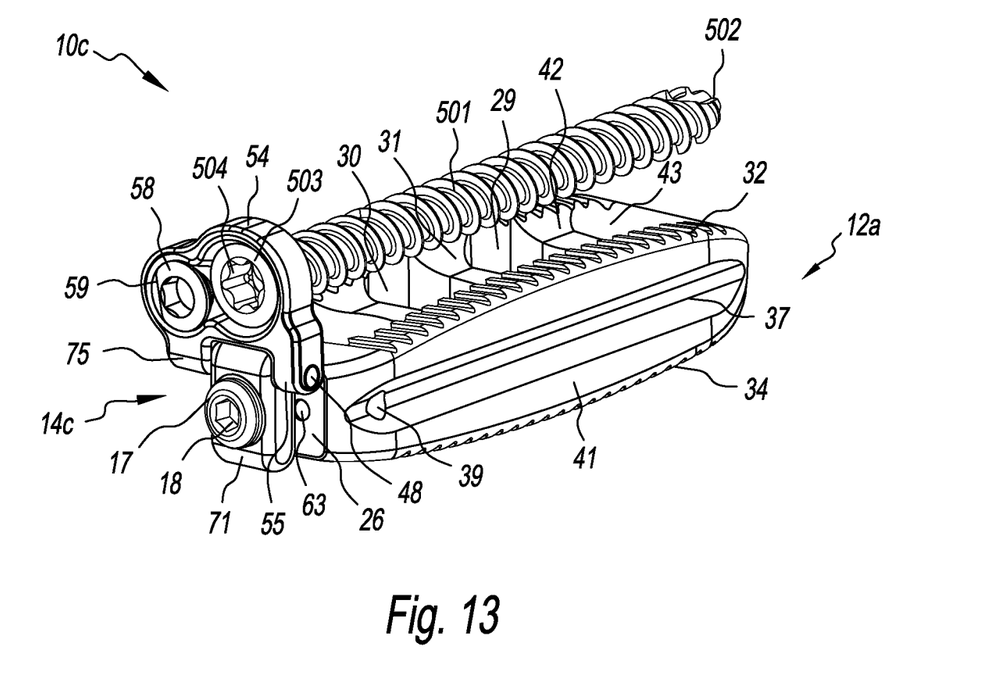
FIG. 13 is a rear side isometric view of the lateral spinal interbody cage and lateral spine plate of FIG. 12, assembled, with the bone screw received in the lateral spine plate and the bone screw nut in the locked position.
Figure 14:
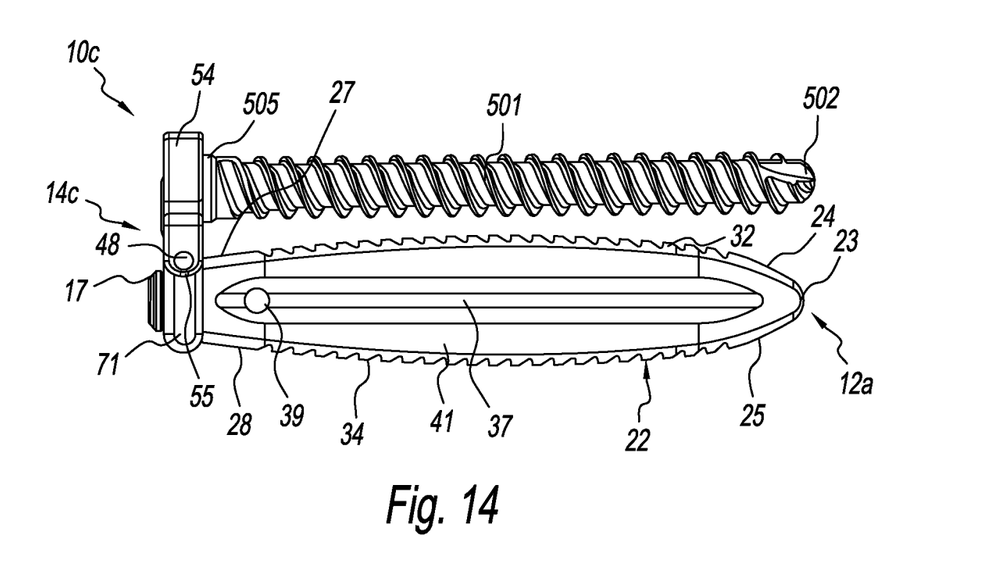
FIG. 14 is a side view of the lateral spinal interbody cage and lateral spine plate of 13.
Figure 15:
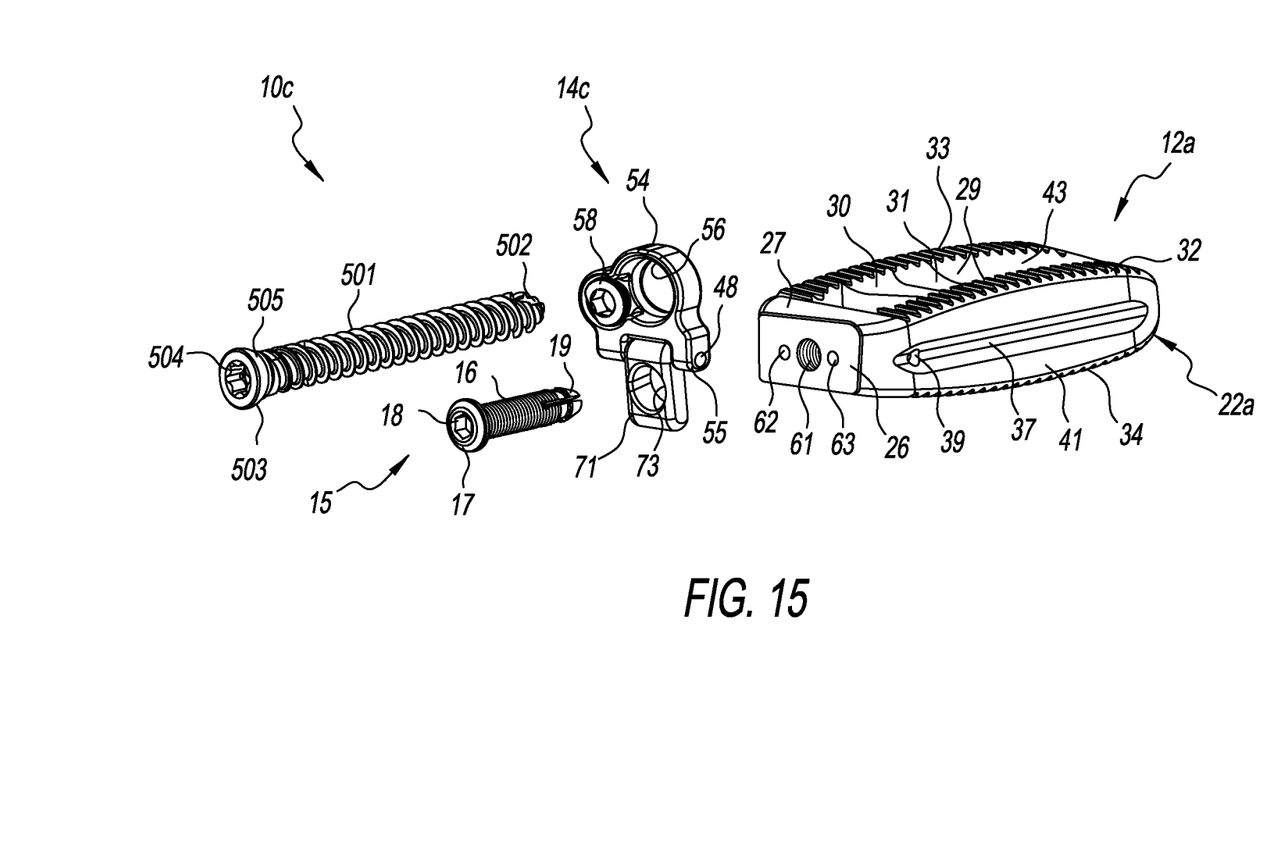
FIG. 15 is an exploded isometric rendering of the lateral spinal interbody cage and lateral spine plate of FIG. 12.
Figure 16:
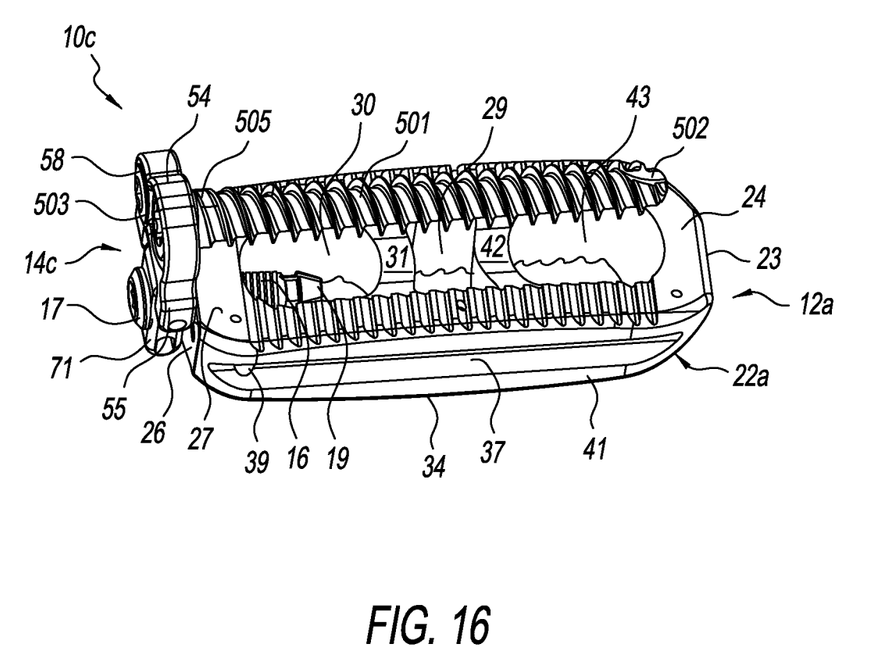
FIG. 16 is a top side rendering of the lateral spinal interbody cage and lateral spine plate of FIG. 12, assembled.

Referring to FIGS. 9-11, there is depicted another exemplary form of a lateral spine implant, generally designated 10b, having another exemplary form of a lateral interbody spine cage 12a and of a lateral spine plate 14b. The components, features, etc. of the lateral interbody spine cage 12a that are the same as the lateral interbody spine cage 12 have the same numbers as the lateral interbody spine cage 12 while the those components, features, etc. that are different have the designation "a" after the number. In like manner, the components, features, etc. of the lateral spine plate 14b that are the same as the lateral spine plate 14 have the same numbers as the lateral spine plate 14 while the those components, features, etc. that are different have the designation "b" after the number. FIG. 9 provides an exploded view of the components of the lateral spine implant 10b, namely the lateral interbody spine cage 12a, the lateral spine plate 14b, and the attachment pin 15, along with two bone screws 500.

The lateral interbody spine cage 12a differs from the lateral interbody spine cage 12 by having three rather than two cavities, namely a rear cavity 30, a middle cavity 29 separated from the rear cavity by a bridge 31, and a front cavity 43 separated from the middle cavity 29 by a bridge 42. Other components, features, etc. are the same.

The lateral spine plate 14b differs from the lateral spine plate 14 by the configuration of its hub and vertebral attachment anus. The lateral spine plate 14b has a hub defined by a first plate 70 having a central hole 72 and a second plate 71 having a central hole 73. The first and second plates 70, 71 are situated back-to-back such that the central holes 72, 73 align for reception of the attachment pin 15. The first (superior) attachment arm 46 has a first boss 55 on one lateral side thereof and a second lateral boss 75 on an opposite lateral side thereof. The hinge pin 48 extends through an upper portion of the first vertebral attachment arm 46 and the first and second lateral bosses 55, 75 to pivotally connect the first vertebral attachment arm 46 to the second plate 71. The second (inferior) attachment arm 45 has a first boss 51 on one lateral side thereof and a second lateral boss 76 on an opposite lateral side thereof. The hinge pin (not seen) extends through a lower portion of the second vertebral attachment arm 45 and the first and second lateral bosses 51, 76 to pivotally connect, the second vertebral attachment arm 45 to the first plate 70. The first and second vertebral attachment arm 46, 45 can pivot/swing into and from a collapsed or closed position from and into an expanded or open position.

Referring to FIGS. 12-16 there is depicted another exemplary lateral spine plate, generally designated 14c, being a variation of the lateral spine plate 14b, the lateral spine plate 14c shown connected to the lateral interbody spine cage 12a together forming a lateral spine implant 10c. The components, features, etc. of the lateral spine plate 14c that are the same as the lateral spine plate 14b have the same numbers as the lateral spine plate 14b while the those components, features, etc. that are different have the designation "c" after the number. The lateral spine plate 14c of FIGS. 12-16 has a single vertebral attachment arm 54 connected to a single hub plate 71, here shown as the upper or superior vertebral attachment arm 54, rather than the two vertebral attachment arms of the lateral spine plate 14b.

Figure 17:
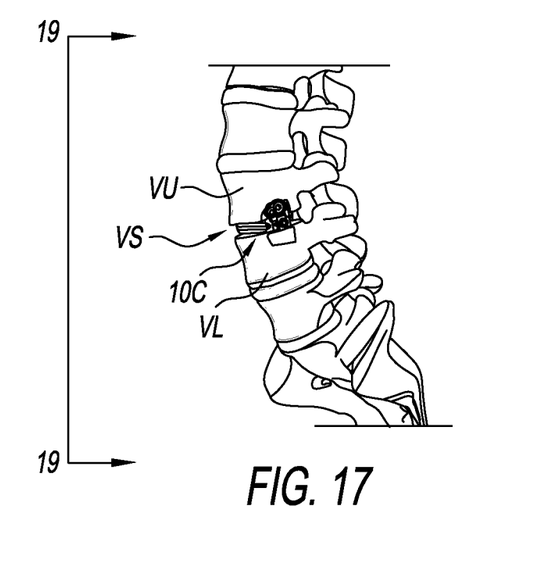
FIG. 17 is an isometric side rendering of a portion of a human spine with the lateral spinal interbody cage of FIGS. 12-16 implanted into the interbody space between upper and lower vertebrae with the lateral spine plate of FIGS. 12-16 attached to the upper vertebra.
Figure 18:
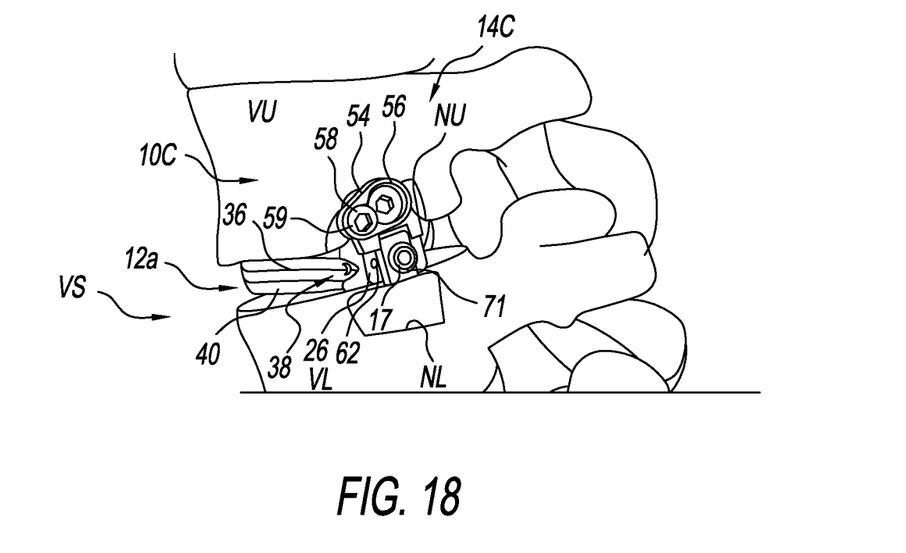
FIG. 18 is an enlarged side view of FIG. 17.
Figure 19:
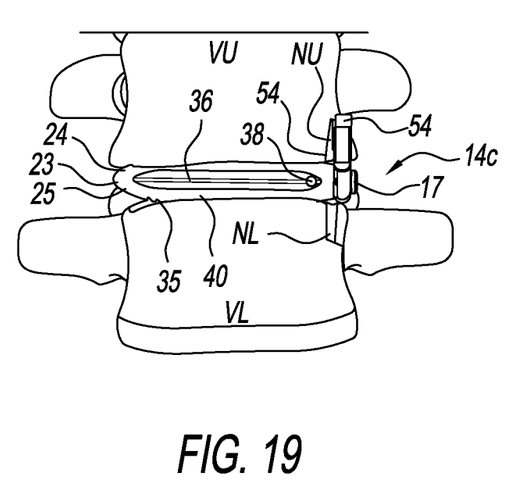
FIG. 19 is a front view of the portion of the spine of FIG. 17 taken along line 19-19 of FIG. 17.

FIGS. 17-19 show a lumbar portion of a human spine wherein the lateral spine implant 10c with the lateral spine plate 14c attached to the lateral interbody cage 12a has been implanted/installed in the vertebral space VS. The vertebral attachment arm 54 has been attached to the upper (superior) vertebra VU within an upper vertebral notch NU. A lower vertebral notch NL in the lower (inferior) vertebra VL is shown for a lower vertebral attachment arm of the lateral spine plate if desired.

It should be appreciated that dimensions of the components, structures, and/or features of the present lateral spine plate implant may be altered as desired within the scope of the present disclosure.

What is claimed is:

1. A spine implant for attachment to a first vertebra and a second vertebra of a spine, the spine implant comprising:
an interbody spine cage comprising a front and a back, an axis defined from the front to the back, and an insertion hole coaxial with the axis, where the interbody spine cage is configured to be inserted at least partially between the first vertebra and the second vertebra;
a first lateral spine plate assembly comprising:
a first plate having a first hole extending through the first plate; and a first arm having a first bone screw bore, a first lateral boss, and a second lateral boss, wherein the first and second lateral bosses of the first plate are spaced apart and receive a portion of the first plate in a pivoting engagement; wherein the first arm is configured to pivot between a first position and a second position, where in the second position the first bone screw bore is parallel with the axis to allow a first bone screw to be received into the lateral side of the first vertebra;
a second lateral spine plate assembly comprising:
a second plate having a second hole extending through the second plate; and a second arm having a second bone screw bore, a first lateral boss, and a second lateral boss, wherein the first and second lateral bosses of the second arm are spaced apart and receive a portion of the second plate in a pivoting engagement; wherein the second arm is configured to pivot between a first position and a second position, where in the second position the second bone screw bore is parallel with the axis to allow a second bone screw to be received into the lateral side of the second vertebra;
and
a connector extending through the first hole, the second hole, and into the insertion hole on the interbody spine cage to couple the first lateral spine plate assembly and the second lateral spine plate assembly to the interbody spine cage.

2. The spine implant of claim 1, further comprising a hinge pin extending through the first lateral boss, the portion of the first plate, and the second lateral boss to pivotally connect the first arm to the first plate.

3. The spine implant of claim 1, wherein the first position is a collapsed condition and the second position is an extended condition.

4. The spine implant of claim 1, further comprising: a first hinge pin extending through the first lateral boss on the first arm, the portion of the first plate, and the second lateral boss on the first arm to pivotally connect the first arm to the first plate; and a second hinge pin extending through the first lateral boss on the second arm, the portion of the second plate, and the second lateral boss on the second arm to pivotally connect the second arm to the second plate.

5. The spine implant of claim 1, wherein the first position of both the first arm and the second arm is a collapsed condition, and the second position of both the first arm and the second arm is an extended condition.

6. The spine implant of claim 1, wherein the first lateral spine plate assembly further comprises a first cam lock and the second lateral spine plate assembly includes a second cam lock; wherein the first cam lock is located adjacent the first bone screw bore and configurable to prevent egress of the first bone screw when received in the first bone screw bore, and the second cam lock is located adjacent the second bone screw bore and configurable to prevent egress of the second bone screw when received in the second bone screw bore.

7. The spine implant of claim 1, wherein the connector comprises a threaded shaft, a head at a first end of threaded shaft, an arrow tip at a second end of the threaded shaft, and one or more slots extending through the arrow tip and at least a portion of the threaded shaft to provide compressibility of the arrow tip when being inserted through the first hole, the second hole, and the insertion hole.

8. The spine implant of claim 1, wherein in the first position the first bone screw bore is non-parallel with the axis.

9. A lateral spine plate for attachment to a lateral side of a vertebra of a spine, the lateral spine plate comprising:
  a body having a front, a back, a top, a bottom, a first lateral side, a second lateral side, an axis defined from the front to the back, and a slot transverse to the axis and extending through the body along the axis from the front to the back;
  a threaded connector situated in the body and extending through the slot, the connector configured to couple the body to an interbody spine implant;
  a first pivot post extending laterally outward from the first lateral side of the body; and
  a first arm pivotally coupled to the body via the first pivot post and pivotable between an expanded position and a collapsed position relative to the body, the first arm having a first bore and a rotating cam lock located in a cam lock bore, wherein the first bore is configured to receive a first bone screw for reception into a first vertebra, wherein the first bore defines an axis that is parallel with the axis of the body in the expanded position to allow the first bone screw to be received into the first vertebra, and wherein the cam lock bore is located adjacent the first bore and the cam lock is rotatable to position the cam lock to prevent egress of the first bone screw when received in the first bore.

10. The lateral spine plate of claim 9, further comprising: a second pivot post extending laterally outward from the second lateral side of the body; wherein the first arm is pivotally coupled to both the first pivot post and to the second pivot post.

11. The lateral spine plate of claim 9, further comprising: a second pivot post extending from the second lateral side of the body; and a second arm having a second bore configured to receive a second bone screw for reception into a second vertebra and coupled to the second pivot post, wherein the second arm is pivotable between an expanded position and a collapsed position relative to the body, and wherein in the expanded position the second bore in the second arm is parallel with the axis to allow the second bone screw to be received into the second vertebra.

12. The lateral spine plate of claim 9, wherein the connector has a threaded shaft configured to be received by the interbody spine implant.

13. The lateral spine plate of claim 12, wherein the connector further includes a resilient head.

14. A spine implant for attachment to a first vertebra and a second vertebra of a spine, the spine implant comprising:
  an interbody spine cage configured to be inserted at least partially between the first vertebra and the second vertebra, the interbody spine cage comprising a front and a back, an axis defined from the front to the back, and an insertion hole coaxial with the axis; and
  a lateral spine plate assembly coupled to the interbody spine cage, the lateral spine plate assembly comprising:
  a body having a front, a back, a top, a bottom, a first lateral side, a second lateral side, an axis defined from the front to the back, and a slot transverse to the axis and extending through the body along the axis from the front to the back; a connector extending through the slot and into the insertion hole of the interbody spine cage, the connector comprising a threaded shaft, a head at a first end of threaded shaft, an arrow tip at a second end of the threaded shaft, and one or more slots extending through a portion of the threaded shaft and the arrow tip to provide compressibility to the portion of the threaded shaft and the arrow tip when being inserted through the insertion hole;
  a first arm coupled to the body and having a first bore configured to receive a first bone screw for reception into the first vertebra, the first arm configured to pivot between a collapsed position and an expanded position relative to the body, wherein the first bore is parallel with the axis in the expanded position to allow the first bone screw to be received into the lateral side of the first vertebra;
  and
  a second arm coupled to the body and having a second bore configured to receive a second bone screw for reception into the second vertebra, the second arm configured to pivot between a collapsed position and an expanded position relative to the body, wherein the second bore is parallel with the axis in the expanded position to allow the second bone screw to be received into the lateral side of the second vertebra.

15. The spine implant of claim 14, wherein the body of the spine plate assembly further comprises: a first pivot post extending from the first lateral side of the body, the first arm coupled to the first pivot post; and a second pivot post extending from the second lateral side of the body, the second arm coupled to the second pivot post.

16. The spine implant of claim 14, wherein the spine plate assembly further comprises a first cam lock and a second cam lock; wherein the first cam lock is located in a first cam bore adjacent the first bore and rotatable to prevent egress of the first bone screw when received in the first bore, and the second cam lock is located in a second cam bore adjacent the second bore and rotatable to prevent egress of the second bone screw when received in the second bore.

* * * * *